(12) United States Patent
Urgaonkar et al.

(10) Patent No.: US 7,642,391 B1
(45) Date of Patent: Jan. 5, 2010

(54) PALLADIUM-CATALYZED COUPLING OF ARYL HALIDES WITH ALKYNES

(75) Inventors: Sameer Urgaonkar, Cambridge, MA (US); John G. Verkade, Ames, IA (US)

(73) Assignee: Iowa State University Research Foundation, Inc., Ames, IA (US)

(*) Notice: Subject to any disclaimer, the term of this patent is extended or adjusted under 35 U.S.C. 154(b) by 887 days.

(21) Appl. No.: 11/364,878

(22) Filed: Feb. 28, 2006

Related U.S. Application Data

(60) Provisional application No. 60/658,492, filed on Mar. 4, 2005.

(51) Int. Cl.
   *C07C 1/26* (2006.01)
(52) U.S. Cl. .................................... 585/469
(58) Field of Classification Search ................ 585/469
   See application file for complete search history.

(56) References Cited

OTHER PUBLICATIONS

Alami, M., et al., "An Efficient Palladium-Catalysed Reaction of Vinyl and Aryl Halides or Triflates With Terminal Alkynes", *Tetrahedron Letters*, 34(40), (1993), 6403-6406.

Alonso, D. A., et al., "A Copper- and Amine-Free Sonogashira-Type Coupling Procedure Catalyzed by Oxime Palladacycles", *Tetrahedron Letters*, 43(51), (2002), 9365-9368.

Böhm, V. P., et al., "Coordination Chemistry and Mechanisms of Metal-Catalyzed C-C Coupling Reactions, 13 / A Copper-Free Procedure for the Palladium-Catalyzed Sonogashira Reaction of Aryl Bromides With Terminal Alkynes at Room Temperature", *European Journal of Organic Chemistry*, 22, (2000), 3679-3681.

Cacchi, S., et al., "Palladium-Catalyzed Reaction of Enol Triflates With 1-Alkynes. A New Route to Conjugated Enynes", *Synthesis*, Issue 04, (Apr. 1986), 320-322.

Calo, V., et al., "Pd Nanoparticles Catalyzed Stereospecific Synthesis of β-Aryl Cinnamic Esters in Ionic Liquids", *Journal of Organic Chemistry*, 68(7), (2003), 2929-2933.

Fukuyama, T., et al., "A Copper-Free Sonogashira Coupling Reaction in Ionic Liquids and Its Application to a Microflow System for Efficient Catalyst Recycling", *Organic Letters*, 4(10), (2002),1691-1694.

Gelman, D., et al., "Efficient Palladium-Catalyzed Coupling of Aryl Chlorides and Tosylates With Terminal Alkynes: Use of a Copper Cocatalyst Inhibits the Reaction", *Angewandte Chemie, International Edition*, 42, (2003), 5993-5996.

Leadbeater, N. E., et al., "Rapid, Easy Copper-Free Sonogashira Couplings Using Aryl Iodides and Activated Aryl Bromides", *Tetrahedron Letters*, 44(48), (2003), 8653-8656.

Méry, D., et al., "A Very Efficient, Copper-Free Palladium Catalyst for the Sonogashira Reaction With Aryl Halides", *Chemical Communications*, (2003), 1934-1935.

Mori, A., et al., "Non-Sonogashira-Type Palladium-Catalyzed Coupling Reactions of Terminal Alkynes Assisted by Silver(I) Oxide or Tetrabutylammonium Fluoride", *Organic Letters*, 2(19), (2000), 2935-2937.

Netherton, M. R., et al., "Air-Stable Trialkylphosphonium Salts: Simple, Practical, and Versatile Replacements for Air-Sensitive Trialkyphosphines. Applications in Stoichiometric and Catalytic Processes", *Organic Letters*, 3(26), (2001), 4295-4298.

Reetz, M. T., et al., "Redox-Controlled Size-Selection Fabrication of Nanostructured Transition Metal Colloids", *Advanced Materials*, 11(9), (1999), 773-777.

Rossi, R., et al., "Palladium- And/Or Copper-Mediated Cross-Coupling Reactions Between 1-Alkynes and Vinyl, Aryl, 1-Alkynyl, 1,2_Propadienyl, Propargyl and Allylic Halides or Related Compounds. A Review", *Organic Preparations and Procedures International*, 27, (1995), 129-160.

Siemsen, P., et al., "Acetylenic Coupling: A Powerful Tool in Molecular Construction", *Angewandte Chemie, International Edition*, 39, (2000), 2632-2657.

Sonogashira, K., et al., "A Convenient Synthesis of Acetylenes : Catalytic Substitutions of Acetylenic Hydrogen With Bromoalkenes, Iodoarenes, and Bromopyridines", *Tetrahedron Letters*, 16(50), (1975), 4467-4470.

Sonogashira, K., "Development of Pd-Cu Catalyzed Cross-Coupling of Terminal Acetylenes With $sp^2$-Carbon Halides", *Journal of Organometallic Chemistry*, 653, (2002), 46-49.

Tykwinski, R. R., "Evolution in the Palladium-Catalyzed Cross-Coupling of sp-and $sp^2$-Hybridized Carbon Atoms", *Angewandte Chemie, International Edition*, 42, (2003), 1566-1568.

Widegren, J. A., et al., "Is It Homogeneous or Heterogeneous Catalysis? Identification of Bulk Ruthenium Metal as the True Catalyst in Benzene Hydrogenations Starting With the Monometallic Precursor, $Ru(II)(\eta^6-C_6Me_6)(OAc)_2$, Plus Kinetic Characterization of the Heterogeneous Nucleation, Then Autocatalytic Surface-Growth Mechanism of Metal Film Formation", *Journal of the American Chemical Society*, 125, (2003), 10301-10310.

*Primary Examiner*—Thuan Dinh Dang
(74) *Attorney, Agent, or Firm*—Schwegman, Lundberg, & Woessner, P.A.; Michael H. Haukaas

(57) ABSTRACT

A method is provided to couple an aryl halide to an alkyne comprising reacting a compound of the formula ArX, wherein Ar is a substituted or unsubstituted aryl group and X is I or Br, with a compound of the formula $HC{\equiv}C-R^1$ wherein $R^1$ is a substituted or unsubstituted organic group, in the presence of an effective amount of a phosphine-free, oxime-free palladium catalyst; $(C_1-C_4)$alkyl $N^+(^-OAc)$ or an alkali metal carbonate, to yield a compound of the formula $Ar-C{\equiv}C-R^1$, wherein the reaction is carried out in the absence of an organic amine or copper(I).

9 Claims, No Drawings

PALLADIUM-CATALYZED COUPLING OF ARYL HALIDES WITH ALKYNES

RELATED APPLICATIONS

This application claims priority under 35 U.S.C. §119(e) from U.S. Provisional Application Ser. No. 60/658,492, filed Mar. 4, 2005, which is incorporated herein by reference.

GOVERNMENT FUNDING

The present invention was made with the support of United States Department of Agriculture Contract No. NRCS 68-3A75-3-146. The U.S. Government has certain rights in the invention.

BACKGROUND OF THE INVENTION

The palladium-catalyzed reaction of aryl halides with terminal alkynes, known as the Sonogashira reaction, constitutes an important aspect of alkyne as well as of organopalladium chemistry.[1,2] This reaction is generally co-catalyzed by Cu(I), and an amine as a base and a phosphine as a ligand for palladium are also typically included.[3] An important side reaction encountered with the presence of a Cu(I) co-catalyst is the Glaser-type oxidative dimerization of the alkyne.[4] To address this issue, several reports have described copper-free Sonogashira reactions, but none of them are free of an amine and a ligand simultaneously, while also operating at room temperature. For example, in 1986, Cacchi et al. reported the coupling of enol triflates with terminal alkynes under copper-free conditions, but a phosphine-ligated palladium precursor and a temperature of 60° C. was employed.[5] In 1993, Linstrumelle published a paper on the Pd-catalyzed coupling of aryl or vinyl halides (I, Br, OTf) with terminal alkynes.[6] In this report, only one example of a phosphine and copper-free (but not amine-free) Sonogashira coupling of a vinyl iodide with a terminal alkyne was described and the coupling proceeded in only moderate yield (57%). For an aryl iodide (only iodobenzene was used), a phosphine-ligated palladium source was included under copper-free conditions. In both cases, 5 mol % palladium catalyst was employed.

Herrmann reported a procedure for the Sonogashira reaction of aryl bromides, but it was necessary to use air-sensitive and pyrophoric P(t-Bu)$_3$ as a ligand, although the coupling did proceed with only 0.5 mol % of palladium and ligand.[7] It is worthy of mention that P(t-Bu)$_3$ can be replaced with the air-stable [(t-Bu)$_3$PH]BF$_4$ in Sonogashira couplings.[8] Ryu described a Sonogashira method for coupling aryl iodides in ionic liquids, but it required an elevated temperature (60° C.) as well as the use of a phosphine ligand.[9]

Recently, Nájera has disclosed a palladacycle catalyst for the cross-coupling of aryl iodides and terminal alkynes.[10] However, this methodology requires relatively harsh conditions (110° C.) and a multi-step synthesis of the catalyst, which is a benzophenone oxime. TBAF, TBAOH, and Ag$_2$O were used by Mori as activators for the Sonogashira coupling of aryl iodides, but an elevated temperature (60° C.) and a phosphine-based palladium-catalyst were needed in all three cases.[11] Moreover, use of a silver catalyst not only would add cost to the catalyst but also to the expense of metal waste disposal/recovery.

Astruc described the use of a preformed Pd(II)-phosphine catalyst for a Sonogashira coupling of aryl halides in neat Et$_3$N.[12] Leadbeater has reported a copper-free Sonogashira methodology for aryl iodides and activated aryl bromides with the traditional palladium catalyst Pd(PPh$_3$)$_2$Cl$_2$ (4 mol %) at 70° C. in neat piperidine.[13] Interestingly, however, the observation was made that under phosphine and copper-free conditions, neither palladium acetate nor palladium on charcoal catalyzed the aforementioned reaction. More recently, a report by Buchwald has appeared describing the coupling of aryl chlorides and aryl tosylates with terminal alkynes, utilizing a bulky biphenylphosphine ligand under copper and amine-free conditions.[14]

Therefore, there is a continuing need for improved catalyst systems for Sonogashira coupling reactions.

SUMMARY OF THE INVENTION

The present invention provides a method to couple an aryl bromide or an aryl iodide to an organic compound comprising a terminal alkynyl (acetylene) group using a phosphine-free and oxime-free palladium catalyst in the presence of $(C_1-C_4)_4N^+[^-OAc]$ or an alkali metal carbonate and in the absence of a free amine and copper (I). The present invention can be summarized in Scheme 1 below:

Scheme 1

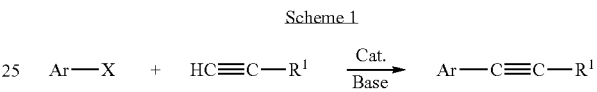

wherein Ar is a substituted or unsubstituted aryl group, such as a $(C_6-C_{14})$aromatic moiety; X is I or Br; $R^1$ is a substituted or unsubstituted organic moiety; Cat. is a phosphine-free oxime-free palladium catalyst, and Base is $((C_1-C_4)$alkyl$)_4$NOAc or an alkali metal carbonate. The reaction does not employ copper (I), or organic amines. Preferably, the reaction is carried out in a suitable organic solvent.

The present invention provides a room temperature, general, and efficient procedure for a ligand, copper, and amine-free Sonogashira reaction of aryl iodides and bromides with terminal alkynes using Pd(OAc)$_2$ or Pd$_2$(dba)$_3$ as the catalyst and tetrabutylammonium acetate as the base. From an industrial as well as an economic standpoint, the present phosphorus-free oxime-free and copper-free process will provide much needed impetus to the development of improved catalyst systems for Sonogashira couplings. Further, the present process is advantageous for synthetic chemists who would generally prefer not to use expensive and sensitive ligands. In addition, the elimination of amines (generally used in large excess) would be welcome because industrial wastes containing them require further treatment before discharge into the environment.

DETAILED DESCRIPTION OF THE INVENTION

Specific and preferred values listed below for aryl moieties, organic moieties, radicals, substituents, and ranges, are for illustration only; they do not exclude other defined values or other values within defined ranges for the radicals and substituents.

Aryl can be phenyl, indenyl, indanyl, naphthyl or anthracenyl; and includes heteroaryl that can be furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl, (or its N-oxide), thienyl, pyrimidinyl (or its N-oxide), 1H-indolyl, isoquinolyl (or its N-oxide) or quinolyl (or its N-oxide).

Specifically, organic moieties ($R^1$) include the following moieties, and/or Aryl (Ar) can be substituted with 1, 2 or 3 of $(C_1-C_6)$alkyl which can be methyl, ethyl, propyl, isopropyl, butyl, iso-butyl, sec-butyl, pentyl, 3-pentyl, or hexyl; ($C_3$-$C_{12}$)cycloalkyl which can be monocyclic, bicyclic or tricyclic and includes cyclopropyl, cyclobutyl, cyclopentyl, cyclohexyl, bicyclo[2.2.2]octanyl, norbornyl, adamantyl as well as various terpene and terpenoid structures; ($C_3$-$C_{12}$)cycloalkyl ($C_1$-$C_6$)alkyl which includes the foregoing cycloalkyl and can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; heterocycloalkyl and (heterocycloalkyl)($C_1$-$C_6$)alkyl which include the forgoing cycloalkyl wherein the cycloalkyl ring system is monocyclic, bicyclic or tricyclic and optionally comprises 1-2 S, non-peroxide O or $N(R^3)$ as well as 2-12 ring carbon atoms; such as morpholinyl, piperidinyl, piperazinyl, indanyl, 1,3-dithian-2-yl, and the like; (the cycloalkyl or heterocycloalkyl ring system optionally includes 1-3 double bonds or epoxy moieties and optionally is substituted with 1-3 OH, ($C_1$-$C_6$)alkanoyloxy, (CO), ($C_1$-$C_6$)alkyl($C_1$-$C_6$)alkoxy or ($C_2$-$C_6$)alkynyl); ($C_2$-$C_6$)alkenyl which can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; halo($C_1$-$C_6$) alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl which can be alkyl substituted with 1 or 2 OH groups, such as hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 3,4-dihydroxybutyl, 1-hydroxypentyl, 5-hydroxypentyl, 1-hydroxyhexyl, or 6-hyroxyhexyl. Ar and/ or $R^1$ can be substituted with 1, 2 or 3 of ($C_1$-$C_6$)alkoxy which can be methoxy, ethoxy, propoxy, isopropoxy, butoxy, isobutoxy, sec-butoxy, pentoxy, 3-pentoxy methylene-dioxy, or hexyloxy; ($C_1$-$C_6$)alkoxycarbonyl which can be methoxycarbonyl, ethoxycarbonyl, propoxylcarbonyl, isopropoxycarbonyl, butoxycarbonyl, pentoxycarbonyl, or hexyloxycarbonyl; ($C_1$-$C_6$)alkylthio which can be methylthio, ethylthio, propylthio, isopropylthio, butylthio, isobutylthio, pentylthio, or hexylthio; ($C_2$-$C_6$)alkanoyloxy can be acetoxy, propanoyloxy, butanoyloxy, isobutanoyloxy, pentanoyloxy, or hexanoyloxy.

Other substituents that can be present on Ar or $R^1$ include 1, 2 or 3 $NO_2$, CN, $N(R^3)(R^4)$ wherein $R^3$ and $R^4$ are each ($C_1$-$C_4$)alkyl, phenyl, benzyl, —$CH_2$—$CH_2$—, —$(CH_2)_3$—, or —$(CH_2)_4$—, Cl, F and the like.

In synthesizing compounds of formula (I), e.g., a product of the reaction described herein, the source of the Pd catalyst is generally employed in an amount of about 0.001-20 mol %, preferably 0.1-10 mol %, based on the aryl halide or alkyne, which can be employed in an about 2-1:1-2 molar ratio. Useful sources of Pd catalyst include Pd(0) catalysts, for example, tris(dibenzylideneacetone) dipalladium(0) ($Pd_2$(dba)$_3$), bis(isonitrile)palladium(0), $PdCl_2(CH_3CN)_2$, [(π-allyl)PdCl]$_2$, bis-(cyclohexylisonitrile) palladium(0), bis(isopropylisonitrile) palladium(0), bis(tert.-butylisonitrile) palladium(0), bis-(p-tolylisonitrile) palladium(0), and bis-(p-methoxyphenyl isonitrile)palladium(0). Other Pd-containing compounds, e.g., Pd(II) compounds, can also be used in the present method. These include $PdCl_2$, palladium(II) carboxylate salts, such as $Pd(OAc)_2$, and $PdBr_2$, $Pd(CN)_2$, $Pd(NO_3)_2$, $PdSO_4$ and the like.

Useful organic solvents including tetrahydrofuran (THF), ethers, glycol ethers, dimethylsulfoxide, dimethylformamide (DMF), acetonitrile, acetamide, toluene, dimethylacetamide and dioxane, and combinations of these solvents, optionally with minor amounts of water, as compatible. Organoamines are not employed, e.g., $N(Et)_3$, piperidine, pyrrolidine and the like.

For preliminary optimization of the reaction conditions, the reaction of electron-rich 4-iodoanisole and 5-hexyn-1-ol in the presence of 2 mol % of $Pd(OAc)_2$ in DMF at room temperature was studied (Scheme 2).

SCHEME 2. Screening of Bases for Sonogashira Coupling of 4-iodoanisole and 5-hexyn-1-ol.

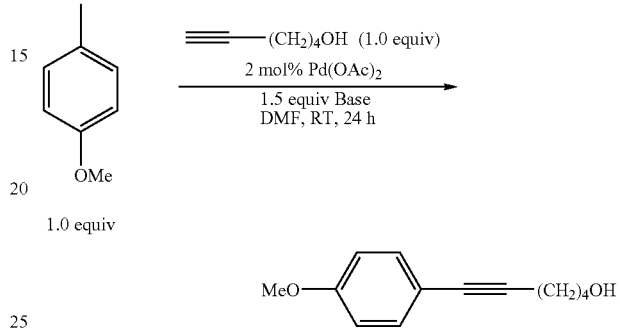

An important initial goal was to find a suitable base that would effect the desired reaction. Surprisingly, commonly used secondary and tertiary amine bases such as triethylamine, DBU (diazabicyclo[5.4.0]undec-7-ene), N-ethyldiisopropylamine (i-$Pr_2$NEt), piperidine, diisopropylamine (i-$Pr_2$NH) as well as $Na_2CO_3$, NaO-t-Bu, and NaOAc gave inferior results, although the carbonates provided moderate yields. Gratifyingly, as shown in Table 1, however, both $Cs_2CO_3$ and $Bu_4NOAc$ were effective as bases, with $Bu_4NOAc$ being the more reactive.

TABLE 1

| entry | base | yield (%)$^a$ |
|---|---|---|
| 1 | $Bu_4NOAc$ | 93$^b$ |
| 2 | $Cs_2CO_3$ | 69 |
| 3 | $Et_3N$ | 5 |
| 4 | DBU | 8 |
| 5 | i-$Pr_2$NEt | 5 |
| 6 | Piperidine | 5 |
| 7 | i-$Pr_2$NH | 10 |
| 8 | $Na_2CO_3$ | 30 |
| 9 | NaO-t-Bu | 0 |
| 10 | NaOAc | 25 |

$^a$Isolated yields (average of two runs).
$^b$Reaction time was 6 hours.

Among the solvents screened (THF, toluene, dioxane, $CH_3CN$, and DMF), DMF proved to be the most efficient. Other palladium sources such as $PdCl_2$, $Pd_2$(dba)$_3$, and [(π-allyl)PdCl]$_2$ are also effective catalysts for the aforementioned reaction.

Using equimolar reactant concentrations, 2 mol % $Pd(OAc)_2$, 1.5 equiv $Bu_4NOAc$, and DMF as the solvent at room temperature, reactions of a series of substituted aryl iodides were carried out via the palladium-catalyzed Sonogashira reaction with phenylacetylene (Table 2).

TABLE 2

Ligand, Copper, and Amine-Free Sonogashira Couplings of Aryl Lodides with Phenylacetylene.

[Reaction scheme: Aryl iodide with R¹ substituent (1.0 equiv) + HC≡C-Ph (1.0 equiv) → with 2 mol % Pd(OAc)$_2$, 1.5 equiv Bu$_4$NOAc, DMF, RT → aryl-C≡C-Ph product with R¹ substituent]

| entry | aryl iodide | product | time (h) | yield (%)[a] |
|---|---|---|---|---|
| 1 | EtO$_2$C-C$_6$H$_4$-I | EtO$_2$C-C$_6$H$_4$-C≡C-Ph | 3 | 96[b] |
| 2 | 4-acetyl-C$_6$H$_4$-I | 4-acetyl-C$_6$H$_4$-C≡C-Ph | 3 | 97[b] |
| 3 | O$_2$N-C$_6$H$_4$-I | O$_2$N-C$_6$H$_4$-C≡C-Ph | 3 | 97[b] |
| 4 | 2-methyl-C$_6$H$_4$-I | 2-methyl-C$_6$H$_4$-C≡C-Ph | 6 | 68 |
| 5 | 3-MeO-C$_6$H$_4$-I | 3-MeO-C$_6$H$_4$-C≡C-Ph | 6 | 73 (80)[c] |
| 6 | 2-OMe-C$_6$H$_4$-I | 2-OMe-C$_6$H$_4$-C≡C-Ph | 6 | 74 (79)[c] |
| 7 | 4-MeO-C$_6$H$_4$-I | 4-MeO-C$_6$H$_4$-C≡C-Ph | 6 | 77 (86)[c] |

[a]Isolated yields (average of two runs).
[b]1 mol % Pd(OAc)$_2$ was employed.
[c]Parenthesized yields are obtained with 3 mol % Pd(OAc)$_2$.

Good to excellent yields were generally obtained under these phosphorus-free, oxime-free, copper (I)-free, and amine-free conditions. Functional groups such as, carboxyethyl, keto, and nitro were well tolerated (Table 2, entries 1-3). Aryl iodides with electron-withdrawing groups gave higher yields than those with electron-neutral or electron-rich groups, and the coupling proceeded with substantially lower palladium catalyst loading. The cross-coupling of sterically hindered aryl iodides (2-iodotoluene and 2-iododanisole) also proceeded quite well (Table 2, entries 4 and 6). As expected, no homo-coupling product was detected by GC under these conditions. It may be noted that while the reactions of aryl iodides possessing electron-withdrawing groups were completed in 3 hours the electron-neutral and electron-rich aryl iodides reacted in 6 hours.

In an effort to further expand the scope of the present oxime-free, phosphorus-free, copper (I)-free, and amine-free Sonogashira reaction, the reaction of substituted aryl iodides with a series of aliphatic terminal alkynes was investigated as summarized in Table 3. The yields were generally higher than those obtained when phenylacetylene was used as the reaction partner. Unfunctionalized alkynes, for example, 1-octyne in Table 3 (entries 2, 3, 6, and 13) as well as functionalized alkynes bearing a hydroxy group (entries 4, 8, 10, 12, and 15), a chloride group (entry 14), a cyano group (entry 18), or a TIPS group (entry 17) reacted efficiently with various aryl iodides to afford the corresponding aryl alkynes in excellent yields. Even a terminal alkyne with an alkene functionality underwent Sonogashira coupling in good yields (entries 1, 5, 7, 9, 11, and 16).

TABLE 3

Ligand, Copper, and Amine-Free Sonogashira Couplings of Aryl Iodides with Aliphatic Terminal Alkynes.[a]

| entry | aryl iodide | alkyne | product | time (h) | yield (%)[b] |
|---|---|---|---|---|---|
| 1 | 4-iodoacetophenone | ethynylcyclohexene | 4-(cyclohex-1-en-1-ylethynyl)acetophenone | 3 | 90[c] |
| 2 | | ≡—(CH₂)₅Me | 4-(oct-1-yn-1-yl)acetophenone | 3 | 94[c] |
| 3 | 4-iodonitrobenzene | ≡—(CH₂)₅Me | O₂N—C₆H₄—≡—(CH₂)₅Me | 3 | 96[c] |
| 4 | | ≡—(CH₂)₄OH | O₂N—C₆H₄—≡—(CH₂)₄OH | 3 | 98[c] |
| 5 | | ethynylcyclohexene | O₂N—C₆H₄—≡—cyclohexenyl | 3 | 97[c] |
| 6 | 2-iodotoluene | ≡—(CH₂)₅Me | 2-methylphenyl—≡—(CH₂)₅Me | 6 | 95 |
| 7 | | ethynylcyclohexene | 2-methylphenyl—≡—cyclohexenyl | 6 | 96 |
| 8 | | ≡—(CH₂)₄OH | 2-methylphenyl—≡—(CH₂)₄OH | 6 | 89 |
| 9 | 3-iodoanisole | ethynylcyclohexene | 3-MeO-phenyl—≡—cyclohexenyl | 6 | 70 (81)[d] |
| 10 | | ≡—(CH₂)₄OH | 3-MeO-phenyl—≡—(CH₂)₄OH | 6 | 85 |
| 11 | 2-iodoanisole | ethynylcyclohexene | 2-MeO-phenyl—≡—cyclohexenyl | 6 | 75 (86)[d] |
| 12 | | ≡—(CH₂)₄OH | 2-MeO-phenyl—≡—(CH₂)₄OH | 6 | 77 (86)[d] |

TABLE 3-continued

Ligand, Copper, and Amine-Free Sonogashira Couplings of Aryl Iodides with Aliphatic Terminal Alkynes.[a]

| entry | aryl iodide | alkyne | product | time (h) | yield (%)[b] |
|---|---|---|---|---|---|
| 13 | | ≡—(CH$_2$)$_5$Me | 2-MeO-C$_6$H$_4$—C≡C—(CH$_2$)$_5$Me | 6 | 93 |
| 14 | MeO-C$_6$H$_4$—I | ≡—(CH$_2$)$_3$Cl | 4-MeO-C$_6$H$_4$—C≡C—(CH$_2$)$_3$Cl | 6 | 80[e] |
| 15 | | ≡—(CH$_2$)$_4$OH | 4-MeO-C$_6$H$_4$—C≡C—(CH$_2$)$_4$OH | 6 | 93 |
| 16 | | ≡—cyclohexenyl | 4-MeO-C$_6$H$_4$—C≡C—cyclohexenyl | 6 | 76 (84)[d] |
| 17 | | ≡—TIPS | 4-MeO-C$_6$H$_4$—C≡C—TIPS | 6 | 97 |
| 18 | | ≡—(CH$_2$)$_3$CN | 4-MeO-C$_6$H$_4$—C≡C—(CH$_2$)$_3$CN | 6 | 87[e] |

[a] For reaction conditions, see Table 1.
[b] Isolated yields (average of two runs).
[c] 1 mol % Pd(OAc)$_2$ was employed.
[d] Parenthesized yields were obtained with 3 mol % Pd(OAc)$_2$.
[e] Pd$_2$(dba)$_3$ was used in place of Pd(OAc)$_2$.

The efficiency of aryl bromides as a coupling partner under P-, oxime-, copper-, and amine-free conditions was also studied (Table 4).

TABLE 4

Ligand, Copper, and Amine-Free Sonogashira Couplings of Aryl Bromides with Terminal Alkynes.

R-C$_6$H$_4$-Br (1.0 equiv) + ≡—R$^1$ (1.0 equiv) → R-C$_6$H$_4$—C≡C—R$^1$
2 mol % Pd$_2$(dba)$_3$, 1.5 equiv Bu$_4$NOAc, DMF, RT

| entry | aryl bromide | product | time (h) | yield (%)[a] |
|---|---|---|---|---|
| 1 | O$_2$N—C$_6$H$_4$—Br | O$_2$N—C$_6$H$_4$—C≡C—Ph | 5 | 86 |
| 2 | | O$_2$N—C$_6$H$_4$—C≡C—(CH$_2$)$_4$OH | 5 | 92 |
| 3 | | O$_2$N—C$_6$H$_4$—C≡C—(CH$_2$)$_5$Me | 5 | 91 |

TABLE 4-continued

Ligand, Copper, and Amine-Free Sonogashira Couplings of Aryl Bromides with Terminal Alkynes.

$$\text{R}\!-\!\!\!\diagdown\!\!\!\text{Ph}\!-\!\!\text{Br} \quad \xrightarrow[\substack{\text{1.5 equiv Bu}_4\text{NOAc} \\ \text{DMF, RT}}]{\substack{\equiv\!-\!\text{R}^1 \text{ (1.0 equiv)} \\ 2 \text{ mol \% Pd}_2(\text{dba})_3}} \quad \text{R}\!-\!\!\!\diagdown\!\!\!\text{Ph}\!-\!\!\equiv\!-\!\text{R}^1$$

| entry | aryl bromide (1.0 equiv) | product | time (h) | yield (%)[a] |
|---|---|---|---|---|
| 4 | 4-AcC$_6$H$_4$-Br | 4-AcC$_6$H$_4$-C≡C-(CH$_2$)$_5$Me | 5 | 90 |
| 5 | 4-NC-C$_6$H$_4$-Br | 4-NC-C$_6$H$_4$-C≡C-(CH$_2$)$_4$OH | 8 | 94 |
| 6 | | 4-NC-C$_6$H$_4$-C≡C-TIPS | 12 | 89 |
| 7 | | 4-NC-C$_6$H$_4$-C≡C-Ph | 24 | 70 |

[a] Isolated yields (average of two runs).

Although Pd$_2$(dba)$_3$ was employed as the catalyst in these reactions, Pd(OAc)$_2$ was also found to be a suitable palladium precursor. However, this method was effective only for electron-deficient aryl bromides and it required a slightly higher catalyst loading (4 mol % Pd) to provide good to excellent yields of the desired product. Thus, aryl bromides with nitro (entries 1-3), keto (entry 4), and cyano (entries 5-7) functional groups were smoothly coupled with a variety of terminal alkynes.

Presently, the beneficial effect of Bu$_4$NOAc in these reactions is not clear. Undoubtedly, Bu$_4$NOAc acts as a mild base to deprotonate the most acidic hydrogen on the alkyne. In addition, it may facilitate the reduction of Pd(OAc)$_2$ to a catalytically active Pd(0) species. The latter phenomenon has been observed previously by Caló[15] and by Reetz[16] and coworkers, who observed Pd nanoparticle formation, albeit at elevated temperatures. However, the reaction in Scheme 1 proceeds in the presence of mercury, thus supporting a homogeneous catalytic pathway.[17]

A particular role for the tetrabutylammonium cation seems to be precluded because it was found that Me$_4$NOAc can be substituted for Bu$_4$NOAc. On the other hand as expected, the coupling of 4-iodoanisole and 5-hexyn-1-ol did not proceed in the presence of Bu$_4$NBr (TBAB). These results indicate that the acetate anion in combination with a bulky cation plays an important role in promoting such coupling reactions. The oxidative addition of an aryl halide to Pd(0) would give a 12 e$^-$ unstable ArPd(II)X intermediate which could be stabilized by tetrabutylammonium acetate to afford a 16 e$^-$ complex [ArPd(II)X$_3$]$^{2-}$Bu$_4$N$^+$ (X=OAc, and/or I or Br) in which the metal center could be expected to be more stable and more electrophilic thus facilitating its complexation with an alkyne. Deprotonation (by BU$_4$NOAc), isomerization, and product-forming reductive elimination would constitute the remaining steps of the catalytic cycle.

In summary, the present invention provides a method wherein a Pd catalyst such as Pd(OAc)$_2$ or Pd$_2$(dba)$_3$ catalyzes the Sonogashira reaction of aryl iodides and bromides at room temperature (20-25° C.) in the absence of phosphorus (e.g., phosphine) compounds, organoamines, and Cu(I). The choice of tetrabutylammonium acetate as the base is important for obtaining high yields of aryl alkynes. The methodology encompasses a wide variety of functional groups and it is worthwhile noting that the present method employs a relatively low palladium catalyst loading. It is believed that this is the first phosphorus-, copper-, and amine-free method for the cross-coupling of aryl iodides and bromides with terminal alkynes.

EXAMPLE 1

General Procedure for the Sonogashira Reaction

An oven-dried Schlenk flask equipped with a magnetic stirring bar was charged with Bu$_4$NOAc (1.5 mmol) and Pd(OAc)$_2$ (1-3 mol %) or Pd$_2$(dba)$_3$ (2 mol % for aryl bromides) inside a nitrogen-filled glove box. The flask was capped with a rubber septum and then it was removed from the glove box. An aryl iodide or bromide (1.0 mmol) and then DMF (3 mL) were then added and after 5 minutes of stirring, the alkyne (1.0 mmol) was added. Stirring was continued at room temperature under argon for the corresponding reaction times indicated in the Tables, after which the reaction mixture was diluted with water (10 mL) and extracted with diethyl ether (4×10 mL). The combined ether layers were dried over Na$_2$SO$_4$, filtered, concentrated, and purified by alumina gel flash chromatography using hexanes or hexanes/ether to elute the desired coupling product.

LITERATURE CITED

The following publications are incorporated by reference herein, as though fully set forth.

(1) Stang, P. J. In *Modern Acetylene Chemistry*; Diederich, F., Ed.; VCH: Weinheim, Germany, 1995.

(2) Sonogashira, K. In *Metal-Catalyzed Reactions*; Diederich, F., Stang, P. J., Eds.; Wiley-VCH: New York, 1998.
(3) (a) Sonogashira, K.; Tohda, Y.; Hagihara, N. *Tetrahedron Lett.* 1975, 4467. (b) Sonogashira, K. *J. Organomet. Chem.* 2002, 653, 46. (c) Rossi, R.; Carpita, A.; Bellina, F. *Org. Prep. Proc. Ind.* 1995, 129. (d) Tykwinski, R. R. *Angew. Chem., Int. Ed.* 2003, 42, 1566.
(4) Siemsen, P.; Livingston, R. C.; Diederich, F. *Angew. Chem., Int. Ed.* 2000, 39, 2632.
(5) Cacchi, S.; Morera, E.; Ortar, G. *Synthesis* 1986, 320.
(6) Alami, M.; Ferri, F.; Linstrumelle, G. *Tetrahedron Lett.* 1993, 34, 6403.
(7) Böhm, V. P. W.; Herrmann, W. A. *Eur. J. Org. Chem.* 2000, 3679.
(8) Netherton, M. R.; Fu, G. C. *Org. Lett.* 2001, 3, 4295.
(9) Fukuyama, T.; Shinmen, M.; Nishitani, S.; Sato, M.; Ryu, I. *Org. Lett.* 2002, 4, 1691.
(10) Alonso, D. A.; Nájera, C.; Pacheco, M. C. *Tetrahedron Lett.* 2002, 43, 9365.
(11) Mori, A.; Kawashima, J.; Shimada, T.; Suguro, M.; Hirabayashi, K.; Nishihara, Y. *Org. Lett.* 2000, 2, 2935.
(12) Méry, D.; Heuzé, K.; Astruc, D. *Chem. Commun.* 2003, 1934.
(13) Leadbeater, N. E.; Tominack, B. J. *Tetrahedron Lett.* 2003, 44, 8653.
(14) Gelman, D.; Buchwald, S. L. *Angew. Chem., Int. Ed.* 2003, 42, 5993.
(15) Caló, V.; Nacci, A.; Monopoli, A.; Laera, S.; Cioffi, N. *J. Org. Chem.* 2003, 68, 2929.
(16) Reetz, M. T.; Maase, M. *Adv. Mater.* 1999, 11, 773.
(17) Widegren, J. A.; Bennett, M. A.; Finke, R. G. *J. Am. Chem. Soc.* 2003, 125, 10301.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A synthetic method to couple an aryl halide to an alkyne comprising reacting a compound of the formula ArX, wherein Ar is a substituted or unsubstituted aryl group and X is I or Br, with a compound of the formula $HC\equiv C-R^1$ wherein $R^1$ is a substituted or unsubstituted organic group, in the presence of an effective amount of a phosphine-free, oxime-free palladium catalyst, and in the presence of $((C_1-C_4)alkyl)_4N^+(^-OAc)$ or an alkali metal carbonate to yield a compound of formula $Ar-C\equiv C-R^1$, wherein the reaction is carried out in the absence of both an organic amine and copper(I).

2. The method of claim 1 wherein the catalyst is a Pd(II) catalyst.

3. The method of claim 2 wherein the catalyst is $Pd(OAc)_2$ $PdCl_2$ or $Pd_2(dba)_3$.

4. The method of claim 1, 2 or 3 wherein $((C_1-C_4)alkyl)_4N^+(^-OAc)$ is tetrabutyl ammonium acetate.

5. The method of claim 4 wherein the reaction is carried out in an organic solvent.

6. The method of claim 4 wherein the reaction is carried out at about 20-25° C.

7. The method of claim 1, 2 or 3 wherein the molar ratio of ArX to $HC\equiv C-R^1$ is about 1:1.

8. The method of claim 7 wherein Ar is $(C_6-C_{14})$aryl.

9. The method of claim 5 wherein the organic solvent is DMF.

* * * * *